(12) United States Patent
Ramos Pinto Correia Da Silva Carvalho Guerra et al.

(10) Patent No.: US 12,030,891 B2
(45) Date of Patent: Jul. 9, 2024

(54) XANTHONIC COMPOUNDS AND THEIR USE AS ANTIFOULING AGENTS

(71) Applicants: CIIMAR—CENTRO INTERDISCIPLINAR DE INVESTIGACAO MARINHA E AMBIENTAL, Matosinhos (PT); UNIVERSIDADE DO PORTO, Oporto (PT); FACULDADE DE CIENCIAS DA UNIVERSIDADE DE LISBOA, Lisbon (PT)

(72) Inventors: Marta Ramos Pinto Correia Da Silva Carvalho Guerra, Oporto (PT); Madalena Maria De Magalhaes Pinto, Oporto (PT); Vitor Manuel De Oliveira E Vasconcelos, Matosinhos (PT); Joana Reis De Almeida, Matosinhos (PT); Elisabete Ribeiro Silva Geraldes, Lisbon (PT); Maria Emilia Da Silva Pereira De Sousa, Oporto (PT)

(73) Assignees: CIIMAR—CENTRO INTERDISCIPLINAR DE INVESTIGACAO MARINHA E AMBIENTAL, Matosinhos (PT); UNIVERSIDADE DO PORTO, Oporto (PT); FACULDADE DE CIENCIAS DA UNIVERSIDADE DE LISBOA, Lisbon (PT)

( * ) Notice: Subject to any disclaimer, the term of this patent is extended or adjusted under 35 U.S.C. 154(b) by 484 days.

(21) Appl. No.: 17/297,347

(22) PCT Filed: Nov. 18, 2019

(86) PCT No.: PCT/IB2019/059886
§ 371 (c)(1),
(2) Date: May 26, 2021

(87) PCT Pub. No.: WO2020/128674
PCT Pub. Date: Jun. 25, 2020

(65) Prior Publication Data
US 2021/0395264 A1    Dec. 23, 2021

(30) Foreign Application Priority Data
Dec. 17, 2018   (PT) ......................................... 115214

(51) Int. Cl.
C07D 493/04   (2006.01)
A01N 43/90    (2006.01)
C07D 519/00   (2006.01)
C09D 5/16     (2006.01)

(52) U.S. Cl.
CPC ........... *C07D 493/04* (2013.01); *A01N 43/90* (2013.01); *C07D 519/00* (2013.01); *C09D 5/1625* (2013.01)

(58) Field of Classification Search
CPC .... C07D 493/04; C07D 519/00; A01N 43/90; C09D 5/16
USPC ........................................................ 523/122
See application file for complete search history.

(56) References Cited

FOREIGN PATENT DOCUMENTS

WO        2009115051 A1    9/2009
WO     WO-2013105037 A1 *  7/2013    ........... A61K 31/352

OTHER PUBLICATIONS

P. Madalena, et al; Xanthones as inhibitors of growth of human cancer cell lines and their effects on the proliferation of human lymphocytes in vitro; Bioorganic & Medicinal Chemistry: A tetrahedron publication for the rapid dissemination of full original research papers and critical reviews on biomolecular chemistry, medicinal chemistry and related disciplines; vol. 10, No. 12; Dec. 1, 2002; pp. 3725-3730; XP002692638.
A. Palmeira, et al; Insights into the in vitro antitumor mechanism of action of a new pyranoxanthone; Chemical Biology & Drug Design; vol. 76; No. 1; Jul. 4, 2010; pp. 43-58; XP055062309.
Y. Li, et al; Antifouling activity of secondary metabolites isolated from Chinese marine organisms; Marine Biotechnology; vol. 15; No. 5; Apr. 25, 2013; pp. 552-558; XP055677697.
X. Nong, et al; Antifouling compounds from the marine-derived fungus aspergillus terreus SCSGAF0162; Natural Product Communications; vol. 10; No. 6; Jun. 1, 2015; 2 pages; XP055677705.
H. Zhonghui, et al; Anti-HSV-1, antioxidant and antifouling phenolic compounds from the deep-sea-derived fungus*Aspergillus versicolor*SCSIO 41502; Bioorganic & Medicinal Chemistry Letters; vol. 27; No. 4; Jan. 16, 2017; pp. 787-791; XP029906444.
D.B.C. Oliveira, et al.; A new acridone with antifungal properties against *Candida* spp. and dermatophytes, and antibiofilm activity against C. albicans; Journal of Applied Microbiology; vol. 127; No. 5; Jul. 11, 2019; pp. 1362-1372; XP055678840.
International Search Report and Written Opinion for corresponding application PCT/IB2019/059886 dated Apr. 1, 2020.

* cited by examiner

*Primary Examiner* — Deve V Hall
(74) *Attorney, Agent, or Firm* — LUCAS & MERCANTI, LLP

(57) ABSTRACT

Synthetic small molecules from an important class of heterocyclic derivatives and homologs and their use as antifouling agents for protection against marine biofouling. The antifouling compounds disclosed herein are environmentally friendly and are able to reduce marine biofouling without inducing toxic effects to target and non-target species. The claimed antifouling compounds also possess ability to be incorporated as antifouling additives in polymeric formulations. Thus, allowing its further application for the preparation of antifouling polymeric matrices, such as coatings, with no hazard effects for the environment.

5 Claims, 4 Drawing Sheets

Table 1

| Compound | EC$_{50}$ (µM; µg.ml$^{-1}$) | LC$_{50}$ (µM) | LC$_{50}$/EC$_{50}$ |
|---|---|---|---|
| XP 13 | 4.60; 1.36 | > 500 | 108.70 |
| 3,4dOHx | 11.53; 2.63 | >500 | 43.37 |
| 34MX | 15.79; 4.04 | >200 | 12.6 |
| D3,4 OCH3X | 50.79; 18.91 | >200 | 3.9 |
| D3,4 COOHX | 34.72; 11.95 | >200 | 5.8 |
| XA11 | 14.16; 4.03 | >100 | 7.1 |
| XA12 | 21.83; 6.25 | >100 | 4.5 |
| XA13 | 11.81; 3.19 | >100 | 8.4 |
| XA14 | 22.78; 9.75 | >100 | 4.4 |
| DR5 | 16.152; 5.40 | >200 | 12.4 |
| DR1 | 27.148; 8.15 | >200 | 7.4 |
| XA15 | 17.52; 6.98 | >100 | 5.7 |
| XA18 | 53.84; 21.45 | >100 | 1.9 |
| XA20 | 7.28; 3.03 | >100 | 13.7 |
| XA22 | 3.57; 1.26 | >100 | 28.0 |

FIG. 1

Table 2

| | Artemia mortality rate (%) | |
|---|---|---|
| | 50 µM | 25 µM |
| XP13 | 3.42±1.40 | 3.51±2.29 |
| 3,4dOHx | 5.51±1.83 | 1.09±0.71 |
| D3,4 OCH3X | 0% | 0% |
| D3,4 COOHX | 2.29 ± 1.51 | 1.32 ± 0.89 |
| XA11 | 7.54 ± 3.19 | 4.69 ± 1.92 |
| XA12 | 0% | 6.11 ± 1.90 |
| XA14 | 11.32 ± 2.96 | 6.34 ± 2.16 |
| DR5 | 5.18 ± 2.82 | 5.40 ± 3.59 |
| XA15 | 4.66 ± 2.46 | 6.60 ± 1.59 |
| XA18 | 2.46 ± 1.69 | 8.96 ± 2.37 |
| XA22 | 6.52 ± 3.60 | 9.07 ± 4.27 |

FIG. 2

XANTHONIC COMPOUNDS AND THEIR USE AS ANTIFOULING AGENTS

CROSS-REFERENCE TO RELATED APPLICATIONS

This application is a 371 of PCT/IB2019/059886, filed Nov. 18, 2019, which claims the benefit of Portuguese Patent Application No. 115214, filed Dec. 17, 2018, each of which are incorporated herein by reference.

TECHNICAL FIELD

This application relates to xanthonic compounds as antifouling agents.

BACKGROUND ART

Biofouling is the temporary or permanent adhesion of organisms on water submerged man-made surfaces. It starts by the adsorption of a molecular film and particles few minutes after immersion, followed by bacteria, cyanobacteria, unicellular algae and protozoa colonization (microfouling) in the following hours, forming a biofilm. These organisms release biochemical cues, adsorbed to surfaces or in solution, that transmit specific information to the environment. Such cues reach conspecifics or organisms of other species, inducing settlement, attachment and metamorphosis of macrofoulers, or otherwise, inhibiting their attachment (Fusetani, 2004, 2011; Callow and Callow, 2002).

To identify settlement-inhibitory compounds and disclose their molecular basis of action is paramount to deal with biofouling and the production of antifouling coatings. Maritime industries spend billions of euros annually to control biofouling, which constitutes an economic burden for shipping and aquaculture, and also to non-maritime industries such as paper manufacturing, food processing, underwater construction, power plants, etc. (Schultz et al., 2011). These coatings may also have medical applications and in general, apply to every activity that requires septic surfaces. Natural alternatives including primary or secondary metabolites from a multitude of species have been found to inhibit the settlement of different biofouling species (Almeida and Vasconcelos, 2015).

To discover non-toxic and environmentally benign antifoulants, substances extracted from various marine organisms have been investigated, particularly polyketide-related compounds (Qian et al., 2015).

Xanthone polyketide-derived compounds represent a class of marine natural compounds with interesting biological effects (Pinto et al., 2005). Several members were found to have antimicrobial activity and weak brine shrimp (*Artemia salina*) toxicity (Sun et al., 2013). Recently, a natural xanthone, isolated from a marine-derived fungus *Aspergillus terreus*, revealed a potent antifoulant effect against the larvae of the barnacle *Balanus amphitrite* (Nong et al., 2015). Xanthones are considered as "privileged structures" (Pinto et al., 2005) which means that the type of substituents and position confer different biological effects to the respective xanthone derivative.

Huang, Z. et al. (2017), disclosed several antioxidant and antifouling phenolic compounds, among which is a xanthonic compound number 13. This compound is not 3,4 substituted as is the case of the present application. Additionally, the cited document has not shown, or proven, to have successful antifouling and antioxidant activity (>50% of inhibition). In fact, this document leads the skilled person into pursuing compounds number 4, 22-24 and 27 as potent natural antifouling compounds which have different chemical structures than those disclosed in the present application.

Blunt, L. et al. (2013) have disclosed several marine natural products, including a few compounds numbered 236, 237, 238, 465, 466, that might appear similar. These compounds are not in fact xanthones 3,4 substituted as is the case of the present application. Additionally, none of these compounds were described as having antifouling activity.

SUMMARY

The present application relates to compounds of formula (I),

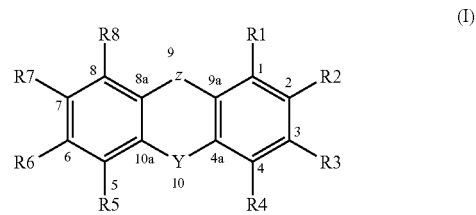

salts or esters thereof, wherein:
Y represents oxygen, sulfur, $CH_2$ or N—H;
Z represents C=O, $CH_2$, CH—OH, C=NOH, C=$NOCH_3$, NO, NOH, S=O or $SO_2$;
R1, R2, R3, R4, R5, R6, R7 and R8 are independently of each other, selected from hydrogen, hydroxyl, alcoxyl, hydroxyalkyl, alkyl, halogen, alkyl-halogen, trifluoromethyl, acetylene, carboxyl, aldehyde, cyano, nitro, $B(OH)_2$, $SO_2NH_2$, aryl or heteroaryl substituted by halogen or hydroxyl or methoxyl, amine, aminoalkoxyl, aminoaryl, imine, methylenealkylamine, cycloalkyl, or together an aminoalkyl, alcoxyl, alkylene (di)oxyl group such as pyran or pyran substituted by alkyl, furan or dioxane or dioxane substituted by aryl, or aryl substituted by halogen or hydroxyl or alcoxyl or alkylene(di)oxyl;
wherein the compounds are 3,4 substituted;
wherein if one of R1 to R8 represents an amine group and/or aminoalkyl this contains counterions such as $HCO_3^-$, $CO_3^{2-}$, $Cl^-$, $NH_2C_6H_4SO_3^-$, 1-$CH_3C_6H_2$-3-OH-4 ($CHCH_3$)-6-$SO_3^-$ which are coordinated or ionically bound in the amine;
wherein at least R3 and R4 are independently selected from hydroxy, optionally substituted C1 to C6 (oxy) alkyl, optionally substituted (oxy)alkylester;
for use as antifouling agents.

In one embodiment the compounds for use as antifouling agents are 3,4-dihydroxy-9H-xanthen-9-one; 3,4-dimethoxy-9H-xanthen-9-one; 3,4-dimethoxy-1-methyl-9H-xanthen-9-one; 12-hydroxy-2,2-dimethyl-3,4-dihydro-2H,6H-pyrano[3,2-b]xanthen-6-one; 3,4-dimethoxy-1-(((2-morpholinoethyl)amino)methyl)-9H-xanthen-9-one; 1-((4-(2-hydroxyethyl)piperazin-1-yl)methyl)-3,4-dimethoxy-9H-xanthen-9-one; 1-((5-amino-3,4-dihydroisoquinolin-2 (1H)-yl)methyl)-3,4-dimethoxy-9H-xanthen-9-one; 3,4-dimethoxy-1-(piperidin-1-ylmethyl)-9H-xanthen-9-one; 1-(dibromomethyl)-3,4-dimethoxy-9H-xanthen-9-one; 3,4-dimethoxy-9-oxo-9H-xanthene-1-carbaldehyde; 1-(hydroxymethyl)-3,4-dimethoxy-9H-xanthen-9-one; dimethyl 2,2'-((9-oxo-9H-xanthene-3,4-diyl)bis(oxy))diacetate and 2,2'-((9-oxo-9H-xanthene-3,4-diyl)bis(oxy))diacetic acid.

The present application also relates to the use of the compounds in the reduction or prevention of marine biofouling.

The present application additionally relates to an antifouling formulation comprising the compound of Formula (I).

The present application also disclosed a polymeric matrix composition comprising the compound of Formula (I) as defined in claim 1 in an amount between 1 and 4% wt.

In one embodiment the matrix is a coating.

DETAILED DESCRIPTION

This application relates to synthetic small molecules from an important class of heterocyclic derivatives and homologs and their use as antifouling agents for protection against marine biofouling. More specifically, the present application relates to xanthonic compounds and derivatives and their use as antifouling agents. The antifouling compounds disclosed herein are environmentally friendly and are able to reduce marine biofouling per-se or when incorporated in polymeric coatings formulations, without inducing toxic effects to target and non-target species and thus with no hazards to the environment.

Particularly, synthetic 3,4-oxygenated xanthones derivates, aminated and not aminated, were investigated for the first time for their antifouling potential.

1. Procedures
1.1 Chemical Synthesis
Synthesis of 3,4-Oxygenated Xanthone Derivatives:

In the context of the present application, the 3,4-oxygenated xanthone derivatives were synthesized according to previously described procedures, as following: 3,4-dihydroxy-9H-xanthen-9-one (3,4dOHx) and 3,4-dimethoxy-9H-xanthen-9-one (34MX) (M. M. Pedro, F. Cerqueira, M. E. Sousa, M. S. J. Nascimento, M. M. M. Pinto. Xanthones as inhibitors of growth of human cancer cell lines and their effects on the proliferation of human lymphocytes in vitro. Bioorganic & Medicinal Chemistry 2002, 10, 3725-3730.); 3,4-dimethoxy-1-methyl-9H-xanthen-9-one (XA13) (D. I. S. P. Resende, P. Pereira-Terra, Â. S. Inácio, P. M. Costa, E. Pinto, E. Sousa, M. M. M. Pinto. Lichen Xanthones as Models for New Antifungal Agents. Molecules 2018, 23, 2617; doi:10.3390/molecules23102617); dimethyl 2,2'-((9-oxo-9H-xanthene-3,4-diyl)bis(oxy))diacetate (D3, 4OCH3X) and 2,2'-((9-oxo-9H-xanthene-3,4-diyl)bis(oxy)) diacetic acid (D3,4 COOHX) (C. Fernandes, K. Masawang, M. E. Tiritan, E. Sousa, V. Lima, C. Afonso, H. Bousbaa, W. Sudprasert, M. Pedro, M. M. Pinto. New chiral derivatives of xanthones: synthesis and investigation of enantioselectivity as inhibitors of growth of human tumor cell lines. Bioorganic Medicinal Chemistry 2014, 22 (3), 1049-1062).

Synthesis of Pyranoxanthone:

The synthesis of pyranoxanthone was performing according to A. Palmeira, A. Paiva, E. Sousa, H. Seca, G. M. Almeida, R. T. Lima, M. X. Fernandes, M. Pinto, M. H. Vasconcelos. *Insights into the in vitro antitumor mechanism of action of a new pyranoxanthone. Chemical Biology & Drug Design* 2010, 76, 43-58.

Synthesis of Aminated Xanthone Derivatives:

The aminated xanthone derivatives were synthesized according to the previously described procedure in Lemos, A.; Gomes, A. S.; Loureiro, J. B.; Brandão, P.; Palmeira, A.; Pinto, M. M. M.; Saraiva, L.; Sousa, M. E. *Synthesis, Biological Evaluation, and In Silico Studies of Novel Aminated Xanthones as Potential p53-Activating Agents. Molecules* 2019.

The investigated compounds presented purity >95% by HPLC-DAD.

1.2 Antifouling Bioactivity
1.2.1 *Mytilus galloprovincialis* Antifouling Bioassays

*M. galloprovincialis* juvenile aggregates were collected from mussel beds at the intertidal rocky shore, during low neap tides at Memória beach, Matosinhos, Portugal, and immediately transported to the laboratory in controlled conditions. Plantigrade larvae (0.5-2 mm) were isolated using a binocular magnifier (Olympus SZX2-ILLT), gently washed in filtered seawater and kept in a petri dish with filtered seawater immediately before the bioassays. Plantigrade larvae showing exploring behavior were selected for the screening bioassay and exposed to the xanthone derivative compounds at 50 µM in 24-well microplates for 15 h, in the darkness at 18±1° C. Test solutions were prepared in filtered seawater and obtained by dilution of stock solutions (50 mM) in DMSO. Four well replicates were used per condition with five larvae per well and 2.5 mL of test solution. A negative control, with DMSO (0.1%) was included in all bioassays, as well as a positive control with 5 µM $CuSO_4$ (a potent AF agent). At the end of the exposure period, the anti-settlement bioactivity was determined by the presence/absence of byssal threads produced by each individual efficiently attached. Compounds showing more than 50% of settlement inhibition at 50 µM were selected for further investigations concerning antifouling effectiveness ($EC_{50}$) and toxicity ($LC_{50}$ and therapeutic index).

1.3 Non-Target Species Toxicity Assessment
1.3.1 *Artemia salina* Lethality Bioassay General toxicity to non-target species was evaluated using the brine shrimp (*Artemia salina*) lethality test (Meyer et al., 1982). *A. salina* cysts were allowed to hatch in nutrient-enriched seawater for approximately 48 hours at 25° C. Newly hatched instar I nauplii were harvested for toxicity test performed in 96-wells microplates with eight replicates per condition and 15-20 nauplii per well. Test solutions of the most promising sulfated antifouling compounds (50 and 25 µM) were prepared in filtered seawater. $K_2Cr_2O_7$ (13.6 µM) was included as positive control and DMSO as negative control. Percentage of mortality was determined at 48 h of exposure.

1.3.2 Luminescent *Vibrio fischeri* Ecotoxicity Assay (ISO11348)

Luminescent *Vibrio fischeri* ecotoxicity assessment (ISO11348) was performed by IK4 TEKNIKER accordingly to the EU hazard assessment of substances and European Ecolabel (ISO 113482). Luminescent *Vibrio fischeri* bacteria test (NRRL-B-11177) was used as a standard test to evaluate the ecotoxicity of the most promising AF compounds. *Vibrio fischeri* bacteria from HACH-LANGE GmbH were grown in laboratory in standard conditions according to guidelines and exposed to a dilution serial of each compound (1000, 500, 250, 125, 62.5 mg/L). After 5, 15 and 30 min of exposure, the light emitted as a by-product of *Vibrio fischeri* cellular respiration was measured at 490 nm. Any inhibition of cellular activity results in a decreased rate of respiration and a corresponding decrease in the rate of luminescence. The decrease of bacterial luminescence measured after 5, 15 or 30 min of exposition was used as test endpoint. Luminescence was measured using a LUMIStox photometer from DR LANGE, after a contact time of 15 min and 30 min at 15±1° C., taking into account a correction factor, fk, which is a measure of intensity change of control samples during the exposure time.

The pH of all samples was within the interval 6.0-8.5. A 2% solution of sodium chloride (NaCl) in deionized water (20 g/L) was used as dilution medium and $K_2Cr_2O_7$ 11.3 µg·mL$^{-1}$) was used as positive control.

1.3.3 Daphnia Acute Immobilization Test (OECD 202)

This test was performed using DAPHTOXKIT F MAGNAT*M. Daphnia magna* are commonly known as water fleas, due to their jumping swimming resemblance to the movement of the fleas. Its short life span and reproductive capabilities make it an ideal organism for analytical use.

The swimming capability of *Daphnia Magna* was assessed after 48 hours of exposure to the diluted testing samples. The *Daphnia* were bred in the laboratory and should be no more than 24 hours old. The number of immobilized *Daphnia* was registered at 24 hours and 48 hours, for the calculation of EL50 and comparison with the control values. The EL50 is the effective concentration of the sample that is expected to cause immobilization to 50% of *Daphnia*.

Note that for this toxicity test, the leaching was obtained only from the WAF method test using the samples and *Daphnia*'s mineral medium as lubricant because standard seawater is harmful to *Daphnia*.

1.3.4. Algae Growth Inhibition Test (OECD 201)

This test was executed using MARINE ALGALTOXKIT™, which contains all the material necessary to perform growth inhibition tests with the marine diatom *Phaeodactylum Tricornutum*.

The species of alga *Phaeodactylum Tricornutum*, were incubated with the testing leaching samples, for 72 hours, in disposable cells of 10 cm path-length. Algal growth or inhibition was registered every 24 hours, measuring the optical density (OD) at 670 nm in the spectrophotometer Jenway 6300, equipped with a holder of 10 cm cells. Having obtained the optical density, it was possible to calculate the EL50, which is the concentration of the test substance that causes a decrease of 50% in the growth of the algae. This terminology is used instead of the standard EC50 when the test material is not completely soluble at the test treat rates.

1.4 Antifouling Mode of Action 1.4.1 Antifouling Targets by Proteomic Analysis

The proteome of *M. galloprovincialis* plantigrade larvae was analyzed based on the method described by Campos et al. (2016). Briefly, proteins from ten *M. galloprovincialis* larvae per replicate were solubilized in lysis buffer with 2% (w/v) SDS, 100 mM Tris-HCl, 0.1 M DTT and protease inhibitor at, pH 7.6. Proteins were subsequently digested following the filter-aided sample preparation (FASP) (Wisniewski et al., 2009). The resulting peptide samples were analysed by nano-LC coupled to a hybrid Ion trap mass spectrometer (LTQ Orbitrap Velos Pro-ETD, Thermo Scientific, Waltham, MA, USA). Full scans were performed at 30000 resolution with scan ranges of 380-2000 m/z and the top 20 most intense ions isolated and fragmented. Collision induced fragmentation (CID) was used to fragment precursor ions. LTQ raw data was first processed in Proteome Discoverer software (version 1.4, Thermo Scientific) and identifications achieved using X!Tandem algorithm in the Scaffold program (version Scaffold 4.3.4, Proteome Software, Portland, Oregon, USA) and using a composite database built with genomic and transcriptomic information from Mollusca species. Protein quantitative analysis was performed using normalized spectral abundance factors (NSAFs) in Scaffold programme and employing non-parametric statistics ($p<0.05$).

1.5 Incorporation of Xanthonic Antifoulants in Marine Coatings

Some of the most potential xanthonic antifoulants were incorporated as antifouling additives in two-component based marine coatings formulations. Two representative marine paints components systems, polydimethylsiloxane (Ref. 87500) and polyurethane (Ref. F0032/95580) based, provided by Hempel A/S were used. For those xanthonic based paint formulations preparation, the proportions by volume of the components used for each paint matrix systems were those recommend by the supplier, 9/1 and 17.8/2.2 of base/curing agent for the polyurethane (PU) and Polydimethylsiloxane (PDMS) systems, respectively. None instead, and depending on the xanthonic chemical functionalities and density, minor adjustments on those proportions were performed, in order to maintain the main coatings properties (e.g. curing time and adhesion). In addition, and to promote the compatibility and homogeneity of the antifoulants in the corresponding polymeric formulations, a prior dissolution step, in accurate pure and dehumidified organic solvents, may be comprised, followed by its addition and blending to the paint components system. The selection and content of the organic solvent must also rely on its compatibility with the components of each polymeric system.

As example, for 1-((5-amino-3,4-dihydroisoquinolin-2 (1H)-yl)methyl)-3,4-dimethoxy-9H-xanthen-9-one (XA20) PDMS based formulations a prior dissolution step in N-methyl-pyrrolidone is suitable, whereas for XA13 is dichloromethane, or mixtures thereof. For 3,4-dihydroxy-9H-xanthen-9-one (3,4 dOHX) based PU formulation a prior dissolution step in N-methyl-pyrrolidone is suitable.

The antifoulant content is determined as a function of the desired final biocide content in the final polymeric formulation (base+curing agent+additives).

The developed antifouling xanthonic based marine coatings were further evaluated in terms of antifoulant incorporation effectiveness by leaching tests (adapted procedure from standard ISO15181). Briefly, acrylic coated substrates are submerged at least for 45 days in artificial seawater, after which quantification of antifoulants release from coatings is provided by HPLC-DAD analyses.

The antifouling effectiveness of xanthonic based marine coating formulations was assessed by an in vivo antisettlement bioassay on coated culture multiwell plates, using *Mytilus galloprovincialis* adhesive mussel plantigrades larvae as target species.

BRIEF DESCRIPTION OF DRAWINGS

For easier understanding of this application, figures are attached in the annex that represent the preferred forms of implementation which nevertheless are not intended to limit the technique disclosed herein.

FIG. 1 shows Table 1 illustrating the antifouling effectiveness versus toxicity of compounds towards the antisettlement of mussel plantigrades. $EC_{50}$, minimum concentration that inhibited 50% of larval settlement; $LC_{50}$ the median lethal dose; $LC_{50}/EC_{50}$, therapeutic ratio. Note: reference values for $EC_{50}<25$ µg·ml$^{-1}$ (U.S. Navy program) and therapeutic ratio ($LC_{50}/EC_{50}$) higher than 15.

FIG. 2 shows Table 2 illustrating the ecotoxicity of compounds towards nauplids of the brine shrimp *Artemia salina*.

BEST MODE FOR CARRYING OUT THE INVENTION

Figure 3:
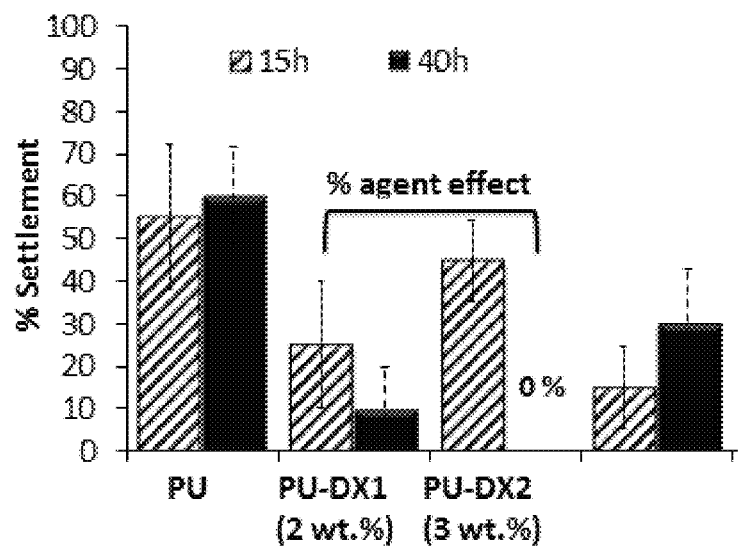
FIG. 3 illustrates the anti-settlement effect of 3,4dOHx-polyurethane based marine paint coatings containing 2 wt. % (PU-DX1) and 3 wt. % (PU-DX2) of xanthone 3,4dOHx against *Mytilus galloprovincialis* larvae settlement. 3,4dOHx, 3,4-dihydroxy-9H-xanthen-9-one.
Figure 4:
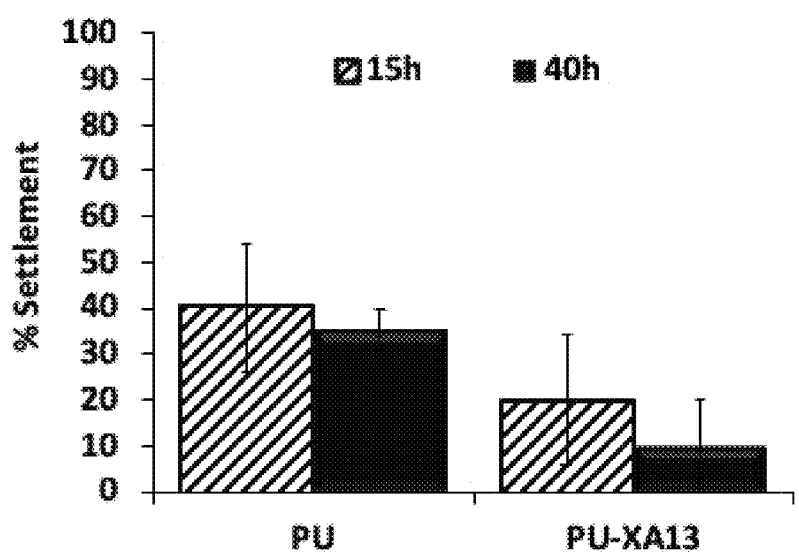
FIG. 4 illustrates the anti-settlement effect of XA13-polyurethane based marine paint coatings containing 1.7 wt. % of XA13 xanthone against *Mytilus galloprovincialis* larvae settlement. XA13, 3,4-dimethoxy-1-methyl-9H-xanthen-9-one.
Figure 5:
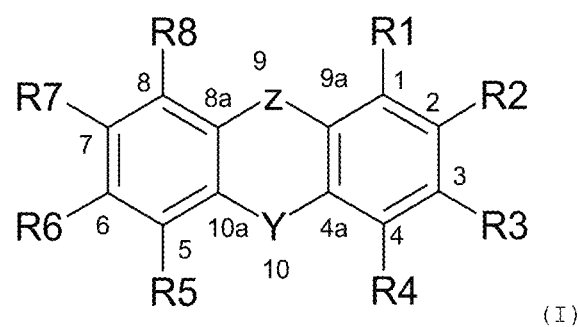
FIG. 5 illustrates the chemical structure of the xanthonic compounds of the present application.

This application relates to synthetic small molecules from an important class of heterocyclic derivatives and homologs and their use as antifouling agents for protection against marine biofouling. More specifically, the present application relates to xanthonic compounds and derivatives and their use as antifouling agents.

Synthetic 3,4-oxygenated xanthones, aminated and not aminated, were investigated for the first time for their antifouling potential.

These xanthones were studied in vivo against the settlement of *Mytilus galloprovincialis* and their mode of action was investigated. Adding to their known pharmacological actions, herein it is disclosed for the first time 3,4-oxygenated xanthonic derivatives, as efficient antifoulants against *Mytilus galloprovincialis* and as compatible agents for commercial polymeric coatings formulations, allowing their use as additives to provide protective antifouling coatings.

The xanthones compounds described herein have the structure represented by Formula I:

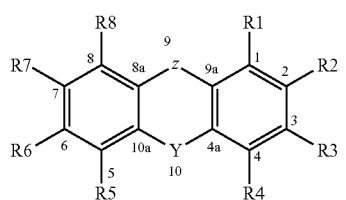

(I)

their salts or esters, wherein:
Y represents oxygen, sulfur, $CH_2$ or N—H;
Z represents C=O, $CH_2$, CH—OH, C=NOH, C=NOCH$_3$, NO, NOH, S=O or $SO_2$;
R1, R1, R3, R4, R5, R6, R7 and R8 are independently of each other selected from hydrogen, hydroxyl, alcoxyl, hydroxyalkyl, alkyl, halogen, alkyl-halogen, trifluoromethyl, acetylene, carboxyl, aldehyde, cyano, nitro, $B(OH)_2$, $SO_2NH_2$, aryl or heteroaryl substituted by halogen or hydroxyl or methoxyl, amine, aminoalkoxyl, aminoaryl, imine, methylenealkylamine, cycloalkyl, or together an aminoalkyl, alcoxyl, alkylene (di)oxyl group such as pyran or pyran substituted by alkyl, furan or dioxane or dioxane substituted by aryl, or aryl substituted by halogen or hydroxyl or alcoxyl or alkylene(di)oxyl;
wherein the compounds are 3,4 substituted;
wherein if one of R1-R8 represents an amine group and/or aminoalkyl this contains counterions such as $HCO_3^-$, $CO_3^{2-}$, $Cl^-$, $NH_2C_6H_4SO_3^-$, 1-$CH_3C_6H_2$-3-OH-4($CHCH_3$)-6-$SO_3^-$ which are coordinated or ionically bound in the amine;
wherein at least R3 and R4 are independently selected from hydroxy, optionally substituted C1 to C6 (oxy) alkyl, optionally substituted (oxy)alkylester.

And the numbers 1, 2, 3, 4, 4a, 5, 6, 7, 8, 8a, 9, 9a, 10 and 10a, represent the numbers of the carbons of Formula I.

1. Results 1.1 Chemical Synthesis

According to the previously described procedures, the following 3,4-oxygenated xanthone derivatives were synthesized: 3,4-dihydroxy-9H-xanthen-9-one (3,4dOHx); 3,4-dimethoxy-9H-xanthen-9-one (34MX); 3,4-dimethoxy-1-methyl-9H-xanthen-9-one (XA13).

The pyranoxanthone 12-hydroxy-2,2-dimethyl-3,4-dihydro-2H,6H-pyrano[3,2-b]xanthen-6-one (XP13) was also obtained.

As well as the following aminated xanthone derivatives: 3,4-dimethoxy-1-(((2-morpholinoethyl)amino)methyl)-9H-xanthen-9-one (XA15); 1-((4-(2-hydroxyethyl)piperazin-1-yl)methyl)-3,4-dimethoxy-9H-xanthen-9-one (XA18); 1-((5-amino-3,4-dihydroisoquinolin-2(1H)-yl)methyl)-3,4-dimethoxy-9H-xanthen-9-one (XA20); 3,4-dimethoxy-1-(piperidin-1-ylmethyl)-9H-xanthen-9-one (XA22); 1-(dibromomethyl)-3,4-dimethoxy-9H-xanthen-9-one (XA14); 3,4-dimethoxy-9-oxo-9H-xanthene-1-carbaldehyde (XA11); 1-(hydroxymethyl)-3,4-dimethoxy-9H-xanthen-9-one (XA12) dimethyl 2,2'-((9-oxo-9H-xanthene-3,4-diyl)bis(oxy))diacetate (D3,4OCH3X) and 2,2'-((9-oxo-9H-xanthene-3,4-diyl)bis(oxy))diacetic acid (D3,4 COOHX).

The investigated compounds presented purity >95% by HPLC-DAD.

The following structures some of the embodiments of the xanthone compounds derived from Formula (I).

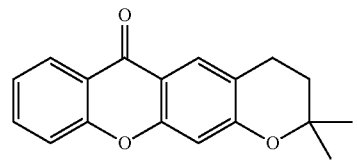

12-hydroxy-2,2-dimethyl-
3,4-dihydro-2H, 6H-
pyrano[3,2-b]xanthen-6-one

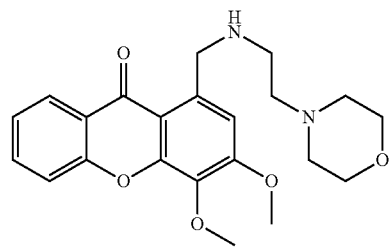

3,4-dimethoxy-1-(((2-
morpholinoethyl)amino)methyl)-
9H-xanthen-9-one

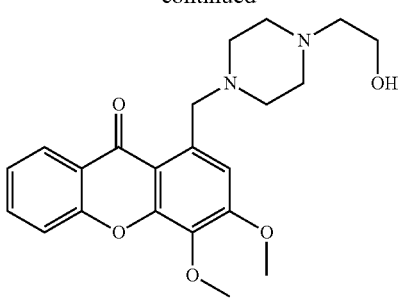

1-((4-(2-hydroxyethyl)piperazin-1-yl)methyl)-3,4-dimethoxy-9H-xanthen-9-one

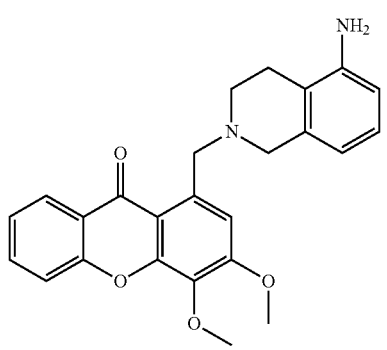

1-((5-amino-3a,4-dihydroisoquinolin-2(1H)-yl)methyl)-3,4-dimethoxy-9H-xanthen-9-one

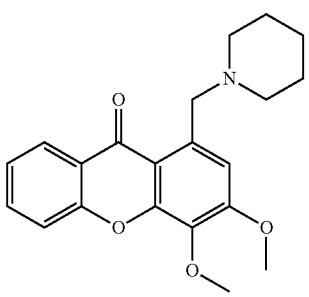

3,4-dimethoxy-1-(piperidin-1-ylmethyl)-9H-xanthen-9-one

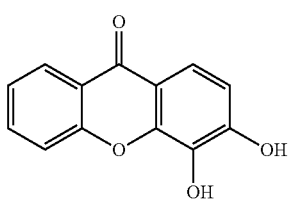

3,4-dihydroxy-9H-xanthen-9-one

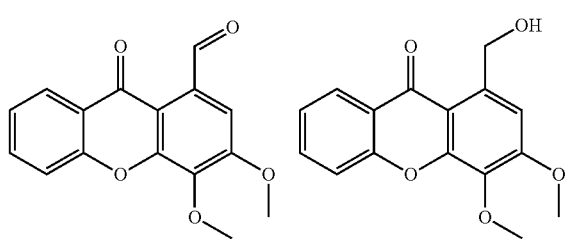

3,4-dimethoxy-9-oxo-9H-xanthen-1-carbaldehyde 1-(hydroxymethyl)-3,4-dimethoxy-9H-xanthen-9-one

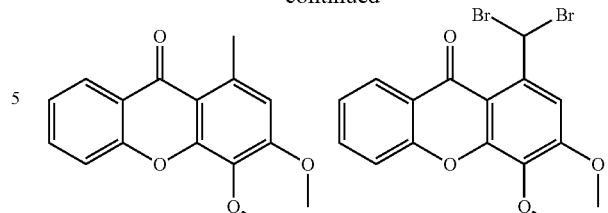

3,4-dimethoxy-1-methyl-9H-xanthen-9-one 1-(dibromomethyl)-3,4-dimethoxy-9H-xanthen-9-one

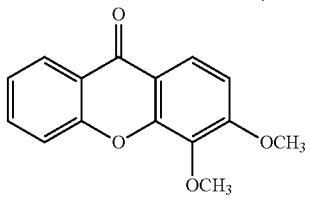

3,4-dimethoxy-9H-xanthen-9-one

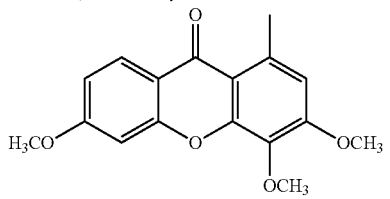

3,4,6-trimethoxy-1-methyl-9H-xanthen-9-one

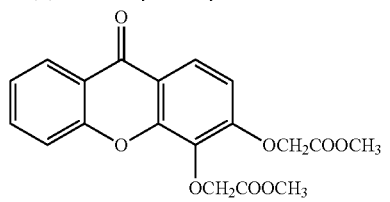

dimethyl 2,2'-((9-oxo-9H-xanthen-3,4-diyl)bis(oxy))diacetate

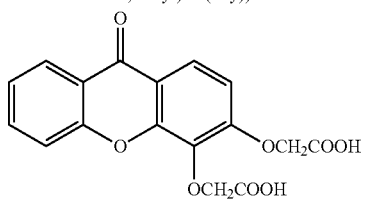

2,2'-((9-oxo-9H-xanthen-3,4-diyl)bis(oxy))diacetic acid

1.2 Antifouling Bioactivity

Dose-response antifouling bioassays confirmed that all compounds showed AF bioactivity towards mussel plantigrade larvae settlement, with levels of effectiveness above the reference values established by the US Navy ($EC_{50} < 25$ µg·ml$^{-1}$) (Table 1).

Regarding toxicity to mussel larvae, no mortality was found in the range of concentrations tested, as so the $LC_{50}$ was considered as higher than the concentration tested for each compound (Table 1).

1.3 Non-Target Species Toxicity Assessment

1.3.1 *Artemia salina* Lethality Bioassay

In the presence of eleven selected xanthones (XP13, 3,4dOHx, D3,4 OCH3X, D3,4 COOHX, XA11, XA12, XA14, DR5, XA15, XA18 and XA22) non-toxic effects were observed, even at 50 µM.

1.3.2 Luminescent *Vibrio fischeri* Assay

Three compounds selected from the initial AF screening did not exert significant general ecotoxicity, as no inhibition of light radiation emitted was found, either after a contact time of 30 min (3,4-dihydroxy-9H-xanthen-9-one (3,4dOHx) LC50>750 μg/mL; 12-hydroxy-2,2-dimethyl-3,4-dihydro-2H,6H-pyrano[3,2-b]xanthen-6-one(XP13) LC50>237 μg/mL; 1-((5-amino-3,4-dihydroisoquinolin-2(1H)-yl)methyl)-3,4-dimethoxy-9H-xanthen-9-one (XA20) LC50>300 μg/mL).

1.3.3 Alga Growth Inhibition Test

The alga growth inhibition of two compounds was tested using *Phaeodactylum tricornutum* (marine alga). This type of diatom is among the most common type of phytoplankton.

Example 1: 3,4-dihydroxy-9H-xanthen-9-one (3,4dOHx) EL50 (72 h)>100 μg/mL-non-toxic Example 2: 1-((5-amino-3,4-dihydroisoquinolin-2(1H)-yl)methyl)-3,4-dimethoxy-9H-xanthen-9-one (XA20) EL50 (72 h)>125 μg/mL-non-toxic.

1.3.4 *Daphnia acute* Immobilization Test

The swimming capability of *Daphnia* in contact with different concentrations of one compound was evaluated. The percentage of immobility at 48 h was determined. 1-((5-amino-3,4-dihydroisoquinolin-2(1H)-yl)methyl)-3,4-dimethoxy-9H-xanthen-9-one (XA20) EL50 (48 h) >300 μg/mL-non-toxic.

1.4 Antifouling Mode of Action 1.4.1 Antifouling Targets by Proteomics

As to provide additional molecular insights on the antifouling properties of 3,4-dihydroxy-9H-xanthen-9-one (3,4dOHx) and 12-hydroxy-2,2-dimethyl-2H,6H-pyrano[3,2-b]xanthone (XP13), the proteome of competent *M. galloprovincialis* plantigrade larvae in response to the antifouling compounds was analyzed by label-free shotgun proteomics. Quantitative protein variations were surveyed employing statistics (non-parametric methods, KW and MW) and hierarchical clustering. Independent statistical tests were performed for each individual compound.

Exposure of larvae to 12-hydroxy-2,2-dimethyl-3,4-dihydro-2H,6H-pyrano[3,2-b]xanthen-6-one (XP13) at 6.25 and 25 uM resulted in the significant change of abundances in 14 proteins. Two putative proximal thread matrix proteins (TMPs) were clearly detected in the control group but become undetected in the two groups exposed to the compound 12-hydroxy-2,2-dimethyl-3,4-dihydro-2H,6H-pyrano[3,2-b]xanthen-6-one(XP13), herein pointing to a significant drop in the expression of these proteins related with the activity of 12-hydroxy-2,2-dimethyl-3,4-dihydro-2H,6H-pyrano[3,2-b]xanthen-6-one(XP13). TMPs are specifically expressed by bivalve mollusks that adhere to underwater surfaces through the production of byssal threads. Their function is to provide viscoelasticity to the byssal threads (Sagert and Waite, 2009). Hence the inhibition of the two TMPs may be pointed as one of the most critical events underlying 12-hydroxy-2,2-dimethyl-3,4-dihydro-2H,6H-pyrano[3,2-b]xanthen-6-one (XP13) inhibition of larvae adhesion.

Finally, 3,4-dihydroxy-9H-xanthen-9-one (3,4dOHx) was, between the 2 antifouling compounds, the one that more alterations induced in the *Mytilus* plantigrade larvae proteome. In total this compound at 12.5 and 50 uM, altered the abundances in 24 proteins, suggesting alterations in a large spectrum of both general and specialized cellular pathways. The results evidence the cellular action of 3,4-dihydroxy-9H-xanthen-9-one (3,4dOHx) particularly towards the functions of cytoskeleton, chaperone mediated regulation of protein activity and cell redox status. Also, two putative collagen proteins, protein-2 collagen-like and pre-collagen P, displayed contrasting patterns of abundance. *Mytilus* collagen proteins (PreCols) are specific to the byssal threads and comprehend the main constituents of this adhesive structure. Moreover, the byssal thread properties such as resistance to tension and shock absorber are essentially provided by these proteins. The adhesion inhibitory effects of 3,4-dihydroxy-9H-xanthen-9-one (3,4dOHx) may well be associated with the change in the abundance of Precols.

In one embodiment, the compounds of formula (I) are used in antifouling formulations. The content of antifouling compound in the formulation is between 1 and 4% wt. in relation to the total weight of the formulation composition.

In another embodiment, the compounds of formula (I) are used in antifouling polymeric matrices compositions as antifouling additives. In this embodiment, the compound is added between 1 and 4% wt. in relation to the total weight of the formulation composition.

In a particular embodiment, the matrix is a two-component polyurethane based marine coating formulation, (Ref. F0032/95580, HEMPEL SA), containing 2 wt. % of incorporated 3,4-dihydroxy-9H-xanthen-9-one (3,4dOHx). The 3,4dOHx is prior dissolved in N-methyl-pyrrolidone (NMP) in a 3,4dOHx/NMP ratio=0.35, followed added and blended in the paint components system, the base and curing agent (base/curing agent ratio=9/1).

2. Antifouling Activity and Incorporation Effectiveness of Xanthonic Based Marine Coatings The antifouling activity of developed xanthonic based marine coatings was assessed in lab conditions against the settlement of the *Mytilus galloprovincialis* larvae and leaching tests were also performed on those formulations. 3,4-Dihydroxy-9H-xanthen-9-one (3,4dOHx) polyurethane-based formulations are an illustrative example of the potential application of the new xanthones. FIG. 1 shown improved antifouling effects when 3,4-dihydroxy-9H-xanthen-9-one (3,4dOHx) is incorporated in a polyurethane (PU) marine paint, with contents as low as 2 wt % a reduction of 55% in the larvae settlement was observed after the first 15 h, which reached a reduction of about 80% after 40 h. In addition, those 3,4-dihydroxy-9H-xanthen-9-one (3,4dOHx) based PU coatings show a low antifoulant leaching from the polymeric matrix, only 0.008% of the incorporated antifoulant leach out after 45 days submerged in artificial seawater. This behavior is associated to the functionality compatibility of this xanthone with the PU matrix.

A similar behavior, although not so pronounced was observed for the xanthone 3,4-dimethoxy-1-methyl-9H-xanthen-9-one (XA13) with 50% reduction of larval settlement in the first 15 h and 29% reduction after 40 h (FIG. 2).

The antifoulant optimum content depends on the specific agent bioactivity and compatibility with the paint components, which can be adjusted taken in account the limitations by each particular polymeric system.

In the foregoing specification, embodiments of the invention have been described with reference to numerous specific details that may vary from implementation to implementation. Thus, the sole and exclusive indicator of what is the invention and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

According to the present invention, the compounds herein disclosed can be used as antifouling agents for protection against marine biofouling, allowing their further application for the preparation of antifouling formulations, and antifouling polymeric matrices, such as coatings, with no hazard effects for the environment.

The invention claimed is:

1. An antifouling formulation comprising the compound of Formula (I)

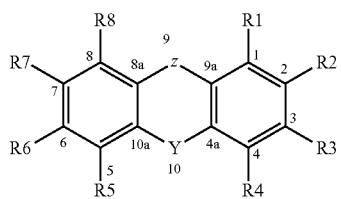

salts or esters thereof,
wherein:
Y represents oxygen, sulfur, $CH_2$ or N—H;
Z represents C=O, $CH_2$, CH—OH, C=NOH, C=$NOCH_3$, NO, NOH, S=O or $SO_2$;
R1, R2, R5, R6, R7 and R8 are independently of each other, selected from hydrogen, hydroxyl, alcoxyl, hydroxyalkyl, alkyl, halogen, alkyl-halogen, trifluoromethyl, acetylene, carboxyl, aldehyde, cyano, nitro, $B(OH)_2$, $SO_2NH_2$, aryl or heteroaryl substituted by halogen or hydroxyl or methoxyl, amine, aminoalkoxyl, aminoaryl, imine, methyelenalkylamine, cycloalkyl, or together an aminoalkyl, alkoxyl, alkylene(di)oxyl group including pyran or pyran substituted by alkyl, furan or dioxane or dioxane substituted by aryl, or aryl substituted by halogen or hydroxyl or alkoxyl or alkylene(di)oxyl;
wherein the compounds are 3,4-substituted;
wherein when one of R1 to R8 represents an amine group and/or aminoralkyl, counterions selected from $HCO_3^-$, $CO_3^{2-}$, $Cl^-$, $NH_2C_6H_4SO_3^-$, 1-$CH_3C_6H_2$-3-OH-4-($CHCH_3$)-6-$SO_3^-$ are coordinated or ionically bound in the amine; wherein at least R3 and R4 are independently selected from hydroxy, optionally substituted C1 to C6 (oxy)alkyl, optionally substituted (oxy)alkylester.

2. A polymeric matrix composition comprising the compound of Formula (I)

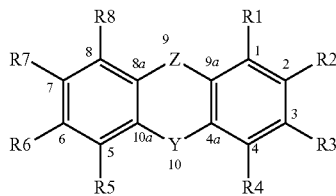

salts or esters thereof,
wherein:
Y represents oxygen, sulfur, $CH_2$ or N—H;
Z represents C=O, $CH_2$, CH—OH, C=NOH, C=$NOCH_3$, NO, NOH, S=O or $SO_2$;
R1, R2, R5, R6, R7 and R8 are independently of each other, selected from hydrogen, hydroxyl, alcoxyl, hydroxyalkyl, alkyl, halogen, alkyl-halogen, trifluoromethyl, acetylene, carboxyl, aldehyde, cyano, nitro, $B(OH)_2$, $SO_2NH_2$, aryl or heteroaryl substituted by halogen or hydroxyl or methoxyl, amine, aminoalkoxyl, aminoaryl, imine, methyelenalkylamine, cycloalkyl, or together an aminoalkyl, alkoxyl, alkylene(di)oxyl group such as pyran or pyran substituted by alkyl, furan or dioxane or dioxane substituted by aryl, or aryl substituted by halogen or hydroxyl or alkoxyl or alkylene(di)oxyl;
wherein the compounds are 3,4-substituted;
wherein when one of R1 to R8 represents an amine group and/or aminoralkyl, counterions selected from $HCO_3^-$, $CO_3^{2-}$, $Cl^-$, $NH_2C_6H_4SO_3^-$, 1-$CH_3C_6H_2$-3-OH-4-($CHCH_3$)-6-$SO_3^-$ are coordinated or ionically bound in the amine;
wherein at least R3 and R4 are independently selected from hydroxy, optionally substituted C1 to C6 (oxy)alkyl, optionally substituted (oxy)alkylester, in an amount between 1 and 4% wt.

3. The polymeric matrix composition according to claim 2, wherein the matrix is a coating.

4. The antifouling formulation according to claim 1, wherein the compound is selected from the group consisting of 3,4-dihydroxy-9H-xanthen-9-one; 3,4-dimethoxy-9H-xanthen-9-one; 3,4-dimethoxy-1-methyl-9H-xanthen-9-one; 12-hydroxy-2,2-dimethyl-3,4-dihydro-2H,6H-pyrano[3,2-b]xanthen-6-one; 3,4-dimethoxy-1-(((2-morpholinoethyl)amino)methyl)-9H-xanthen-9-one; 1-((4-(2-hydroxyethyl)piperazin-1-yl)methyl)-3,4-dimethoxy-9H-xanthen-9-one; 1-((5-amino-3,4-dihydroisoquinolin-2(1H)-yl)methyl)-3,4-dimethoxy-9H-xanthen-9-one; 3,4-dimethoxy-1-(piperidin-1-ylmethyl)-9H-xanthen-9-one; 1-(dibromomethyl)-3,4-dimethoxy-9H-xanthen-9-one; 3,4-dimethoxy-9-oxo-9H-xanthene-1-carbaldehyde; 1-(hydroxymethyl)-3,4-dimethoxy-9H-xanthen-9-one; dimethyl 2,2'-((9-oxo-9H-xanthene-3,4-diyl)bis(oxy))diacetate and 2,2'-((9-oxo-9H-xanthene-3,4-diyl)bis(oxy))diacetic acid.

5. The polymeric matrix composition according to claim 2, wherein the compound is selected from the group consisting of 3,4-dihydroxy-9H-xanthen-9-one; 3,4-dimethoxy-9H-xanthen-9-one; 3,4-dimethoxy-1-methyl-9H-xanthen-9-one; 12-hydroxy-2,2-dimethyl-3,4-dihydro-2H,6H-pyrano[3,2-b]xanthen-6-one; 3,4-dimethoxy-1-(((2-morpholinoethyl)amino)methyl)-9H-xanthen-9-one; 1-((4-(2-hydroxyethyl)piperazin-1-yl)methyl)-3,4-dimethoxy-9H-xanthen-9-one; 1-((5-amino-3,4-dihydroisoquinolin-2(1H)-yl)methyl)-3,4-dimethoxy-9H-xanthen-9-one; 3,4-dimethoxy-1-(piperidin-1-ylmethyl)-9H-xanthen-9-one; 1-(dibromomethyl)-3,4-dimethoxy-9H-xanthen-9-one; 3,4-dimethoxy-9-oxo-9H-xanthene-1-carbaldehyde; 1-(hydroxymethyl)-3,4-dimethoxy-9H-xanthen-9-one; dimethyl 2,2'-((9-oxo-9H-xanthene-3,4-diyl)bis(oxy))diacetate and 2,2'-((9-oxo-9H-xanthene-3,4-diyl)bis(oxy))diacetic acid.

* * * * *